Figure 2:
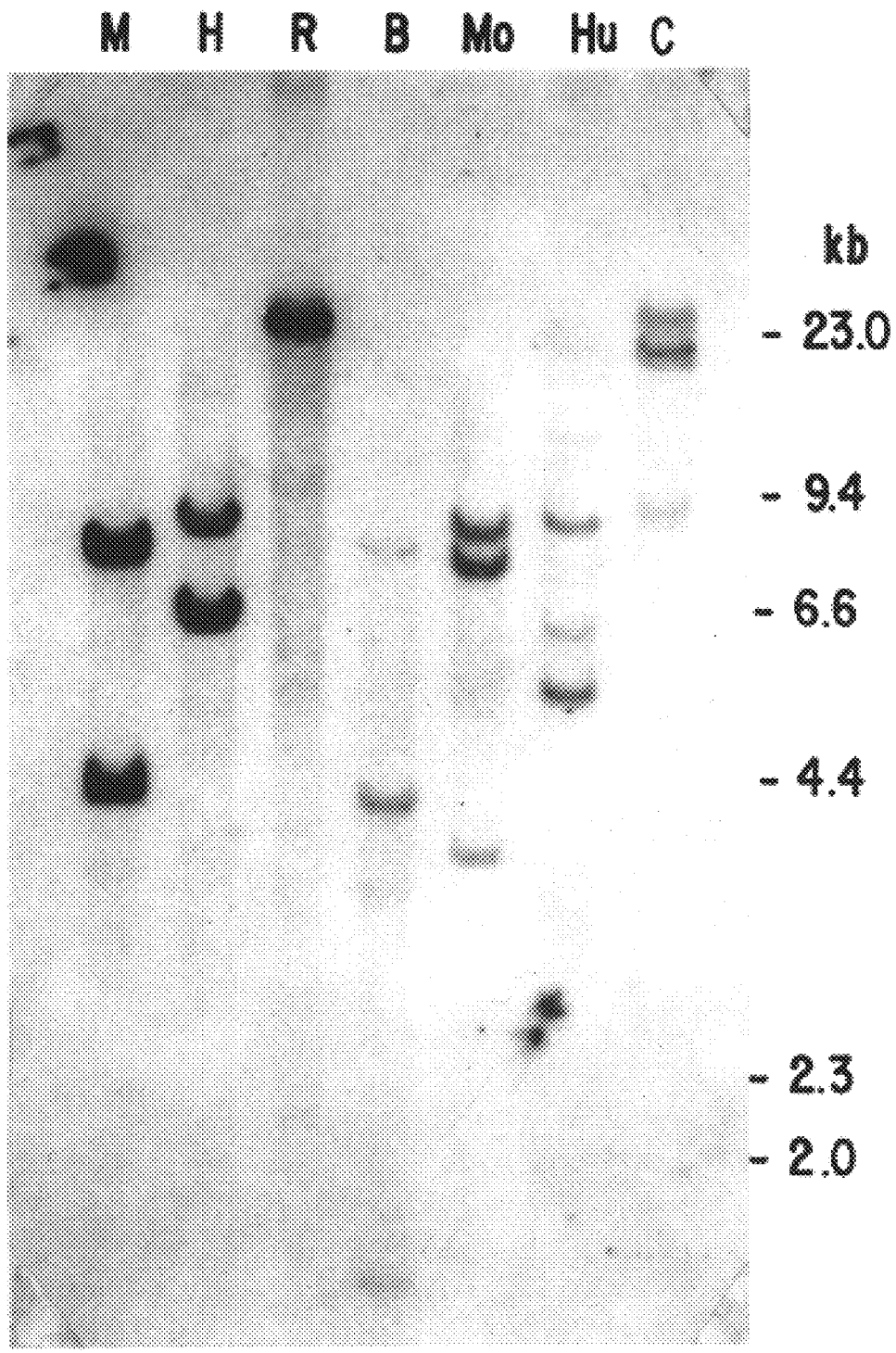

United States Patent [19]
Meruelo et al.

[11] Patent Number: 6,013,441
[45] Date of Patent: Jan. 11, 2000

[54] MAMMALIAN AND HUMAN FXI-T1

[75] Inventors: Daniel Meruelo, Scarborough; Christine L. Pampeno, New York, both of N.Y.

[73] Assignee: New York University, New York, N.Y.

[21] Appl. No.: 08/906,360

[22] Filed: Aug. 5, 1997

Related U.S. Application Data

[60] Provisional application No. 60/023,173, Aug. 5, 1996.

[51] Int. Cl.[7] .............................. C12Q 1/68; C07H 21/02
[52] U.S. Cl. ................................................. 435/6; 536/23.1
[58] Field of Search ................................ 435/6; 536/23.1, 536/23.5, 24.31

[56] References Cited

PUBLICATIONS

Amari, N.M.B., et al., Murine Thymomas Induced by Fractionated–X–Irradiation Have Specific T–Cell Receptor Rearrangements and Characteristics Associated with Day–15 to–16 Fetal Thymocytes. Dec. 1987, vol. 7, No. 12, pp. 4159–4168 Mol. Cell. Biol.

Pampeno, C.L., et al. A Novel cDNA Transcript Expressed in Fractionated X–Irradiation–induced Murine Thymomas. Aug. 1996, vol. 7, pp. 1113–1123. Cell Growth & Differ.

Amari, N.M.B., et al., Effects of fractionized x–irradiation on the Ly–6–Ril–1—Pol–5 region. 1990, vol. 32, pp. 252–262. Immunogenetics.

*Primary Examiner*—Eggerton A. Campbell
*Attorney, Agent, or Firm*—Pennie & Edmonds LLP

[57] ABSTRACT

The present invention concerns the field of molecular genetics and medicine. Particularly, it concerns a gene, FXI-T1, whose mRNA levels are increased in fractionated X-irradiation induced leukemias and methods of using FXI-T1 to classify tissue samples for medical purposes. Specifically, the invention concerns the murine and human homologs of FXI-T1.

10 Claims, 5 Drawing Sheets

SEQ ID NO:1

```
  1 MRPVRRNFYD PSSAPGKGIV WEWENDGGAW TAYDMDICIT IQNAYEKQHP
 51 WLDLSSLGFC YLIYFNSMSQ MNRQTRRRRR LRRRLDLAYP LTVGSIPKSQ
101 SWPVGASSGQ PCSCQQCLLV NSTRAASNAI LASQRRKAPI APAAPPAPPP
151 PPPPLPPGGP PGALVVRPSA TFAGAALWAA PATGPTEPAP PPGVPPRSPS
201 APNGAPTPGQ NNLSRPGPQR STSVSARASI PPGVPALPVK NLNGTGPVHP
251 ALAGMTGILL CAAGLPVCLT RAPKPILHPP PVSKSDVKPV PGVPGVCRKT
301 KKKHLKKSKN PEDVVRRYMQ KVKNPPDEDC TICMERLVTA SGYEGVLRNK
351 SVRPELVGRL GRCGHMYHLL CLVAMYSNGN KDGSLQCPTC KAIYGEKTGT
401 QPPGKMEFHL IPHSLPGFAD TQTIRIVYDI PTGIQGPEHP NPGKKFTARG
451 FPRHCYLPNN EKGRKVLRLL ITAWERRLIF TIGTSNTTGE SDTVVWNEIH
501 HKTEFGSNLT GHGYPDASYL DNVLAELTAQ GVSEAMAKA
```

SEQ ID NO :2

```
   1 CCAGCATCTT TCCCAGCCCC CTTGCCTTTT AAAATTTTAA TTGCTTTTAT
  51 TTATTAATTT ATTGGAGGTC AGATCAAAGC CTGAGGGAAC CGATTCTCTC
 101 CTTCCACCAC GCGGGTCTCT GGGATTAGAA TCTTGTTGTC AGGCTTGGTG
 151 GCAAGCACCT TCCCCTGCTG AGCCATATCG GAGGCCCAGT CTCCATGTCT
 201 TGAATCTCCC TGTCTGCGCT GATCCCCTTC CTGGCTTCGA AGGGTCCCTC
 251 TTGGGGGCCT GTATTGACAT CTCTCTCCCT CCTGAGCACA GGTACCATGC
 301 GGCCGGTGCG ACGCAACTTC TACGATCCAT CGTCGGCGCC GGGCAAGGGC
 351 ATCGTGTGGG AATGGGAGAA CGACGGCGGG GCGTGGACGG CCTACGACAT
 401 GGACATCTGC ATCACCATCC AGAACGCGTA CGAGAAGCAG CACCCGTGGC
 451 TCGACCTCTC ATCGCTCGGC TTCTGCTACC TCATCTACTT CAACAGCATG
 501 TCCCAGATGA ACCGCCAGAC GCGCCGCCGC CGCCGCCTGC GCCGTCGCCT
 551 GGACCTGGCT TACCCGCTCA CTGTCGGCTC CATTCCCAAG TCGCAATCCT
 601 GGCCCGTGGG AGCCAGCTCG GGTCAGCCCT GCTCCTGTCA GCAGTGCCTG
 651 CTGGTCAACA GCACGCGCGC CGCCTCCAAC GCCATCCTGG CCTCGCAGCG
 701 CCGCAAGGCT CCCATTGCGC CAGCCGCGCC TCCAGCGCCC CCTCCGCCCC
 751 CGCCGCCGCT GCCACCCGGA GGACCTCCGG GTGCGCTCGT TGTGCGCCCC
 801 AGCGCCACTT TCGCCGGAGC TGCGCTCTGG GCCGCACCTG CCACCGGCCC
 851 CACGGAGCCT GCGCCGCCTC CAGGAGTTCC CCCAAGGAGC CCTAGTGCCC
 901 CCAACGGAGC GCCCACACCG GGCCAAAACA ACCTCAGTCG ACCAGGACCA
 951 CAGAGGTCCA CCAGCGTCAG CGCACGCGCC TCTATCCCGC CTGGGGTTCC
1001 GGCGCTCCCC GTGAAGAACT TGAATGGCAC TGGCCCTGTC CACCCAGCCT
1051 TGGCAGGGAT GACCGGGATC CTGCTGTGTG CAGCGGGGCT GCCGGTGTGC
1101 CTGACACGAG CACCCAAACC CATCCTGCAC CCACCACCAG TAAGCAAAAG
1151 CGACGTGAAG CCTGTGCCTG GAGTGCCCGG CGTGTGCCGC AAGACCAAGA
1201 AGAAACACC TCAAGAAAAG CAAGAATCCT GAGGATGTGG TTCGGAGGTA
1251 CATGCAGAAG TGAAAAACCC GCCTGATGAG GACTGTACCA TTTGCATGGA
1301 GCGGCTGGTC ACAGCATCTG GCTATGAGGG CGTGCTCCGA AACAAGAGTG
1351 TGCGGCCCGA GCTTGTGGGC CGCCTGGGCC GCTGCGGCCA CATGTATCAC
1401 CTGCTCTGCC TGGTGGCCAT GTACTCCAAT GGCAACAAGG ATGGCAGCCT
1451 GCAGTGTCCA ACCTGCAAAG CCATCTACGG GGAGAAGACA GGGACACAGC
1501 CACCAGGGAA GATGGAGTTT CACCTCATCC CGCACTCGCT GCCTGGTTTT
1551 GCAGACACCC AGACGATCCG CATCGTCTAT GACATCCCCA CGGGCATCCA
1601 GGGCCCTGAA CATCCCAACC CAGGCAAGAA GTTCACAGCC AGAGGCTTCC
```

FIG.1

```
1651 CTCGCCACTG CTACCTACCC AACAATGAGA AGGGCCGAAA GGTGCTGAGA
1701 TTGCTCATCA CCGCCTGGGA ACGCAGACTC ATCTTCACTA TCGGAACATC
1751 CAACACCACG GGCGAGTCGG ACACCGTGGT GTGGAACGAG ATTCACCACA
1801 AGACGGAGTT TGGTTCCAAC CTCACTGGTC ACGGCTACCC CGACGCCAGC
1851 TACCTAGACA ACGTGCTGGC TGAGCTCACC GCCCAGGGGG TTTCTGAGGC
1901 CATGGCCAAG GCCTGAGGCC TGAGTTGCCC GCCTTCCCTT TTGCCTTGCC
1951 TCTAGCCTGG CACATGCCTC CCTCCGCTCT CGGCGGGAGG AGCCAGAAGC
2001 GCTAAGGGGA TCTGGCTGGT GGCTGTGGGG GGGGTGATGG GAGTCCACCA
2051 GGCCAGCTGG CTCCAACCTG TGGCTTCCGG CAAGAGCAGC AGAGATAGGA
2101 CCACCAGCAA GGGCGACTTC CCTATGGAAA ACGATGGCGC TTTGCCCTTC
2151 ACACCACACA CAAACGCACA CGTGTCCTGT TGCACGCACG CACTCACGCA
2201 CGTACACCAC GTGCCTCTCC ACTTCTCCCA GCTTGGGGAG AAAGAGACAG
2251 AAAGGCCCCC ATGACATGTC CTGTGGAAAT ACCTGTGTCT CCATTACATC
2301 TGTATAGGCT CGTCCCTTTC CCAGGACTTG AGTCAAGCAC GGGATAGTGG
2351 GGGGGACTCT GTAAGGCTTC AAGGGGTCGC TCTGCCCCTG GGCCTCAACC
2401 CCTTAACCCA CGTCAGCGCT GCCACCTGCC CACTGAGCAC TGCAAAGCCA
2451 ATGGGGTAGA AACCCCAGGT TATTAAGTAG CTTTTCGCAG GCCACTGGGG
2501 ACGAGGCTAT CTTAACTTTG TGCTTGTGTC TATCTTTCCC GGGACCCTGA
2551 CTTCTTCTTC TTCCTGTGTC CATCTCTTGA CCTCTGTCTA TCCCAGGCAA
2601 AGACATCGTC CTTGCCTCTG TACCGGCTTC TCCCCCACTA AACCGCTCCG
2651 GACATTTGAG ACCCACTTCT GGCTTCAGGA GCGAGGGGAG GAGGCCTTGT
2701 TCAGGCTATA CACGCATCAA GCTGAGCAGG CAGCAAAGCG TTAAACTTCT
2751 CCCTGCTTGA AAGTGGGCGG TGGGCGGCTG ATCGTCTCAG GCCAACCAGA
2801 GGCCCGTTGC CCAGGCAACT CACCAGCTCC GCCTCTGAGG ATTGGCTGCT
2851 GGGATGGAAG TCAGCCAAGC TTTAAAGGGA CGCCAGCAAT TGCTCTTTTG
2901 GAAAAAAAAA AAAAATCTAC CAGTCCCACT GTGGGTGGAG AAATAAATGG
2951 TCTTTCTCCT TAAAA

SEQ ID NO:3

1 AAAATTCCTC TTTCTGGTAA ATAAAGAGGT GGGTGTCACC CTGACCATCT
  51 AAAAAAAAAA AAAAGGTTTT CTCGTTAACG ACCGCAGGGA AATTTCGAAC
 101 CGACTGAAGG TAGGGTCGTC GGTTAGGAGT CTCCGCCTCG ACCACTCAAC
 151 GGACCCGTTG CCCGGAGACC AACCGGACTC TGCTAGTCGG CGGGTGGCGG
 201 GTGAAAGTTC GTCCCTCTTC AAATTGCGAA ACGACGGACG AGTCGAACTA
 251 CGCACATATC GGACTTGTTC CGGAGGAGGG GAGCGAGGAC TTCGGTCTTC
 301 ACCCAGAGTT TACAGGCCTC GCCAAATCAC CCCCTCTTCG GCCATGTCTC
 351 CGTTCCTGCT ACAGAAACGG ACCCTATCTG TCTCCAGTTC TCTACCTGTG
 401 TCCTTCTTCT TCTTCAGTCC CAGGGCCCTT TCTATCTGTG TTCGTGTTTC
 451 AATTCTATCG GAGCAGGGGT CACCGGACGC TTTTCGATGA ATTATTGGAC
 501 CCCAAAGATG GGGTAACCGA AACGTCACGA GTCACCCGTC CACCGTCGCG
 551 ACTGCACCCA ATTCCCCAAC TCCGGGTCCC CGTCTCGCTG GGGAACTTCG
 601 GAATGTCTCA GGGGGGGTGA TAGGGCACGA ACTGAGTTCA GGACCCTTTC
 651 CCTGCTCGGA TATGTCTACA TTACCTCTGT GTCCATAAAG GTGTCCTGTA
 701 CAGTACCCCC GGAAAGACAG AGAAAGAGGG GTTCGACCCT CTTCACCTCT
 751 CCGTGCACCA CATGCACGCA CTCACGCACG CACGTTGTCC TGTGCACACG
 801 CAAACACACA CCACACTTCC CGTTTCGCGG TAGCAAAAGG TATCCCTTCA
 851 GCGGGAACGA CCACCAGGAT AGAGACGACG AGAACGGCCT TCGGTGTCCA
 901 ACCTCGGTCG ACCGGACCAC CTGAGGGTAG TGGGGGGGGT GTCGGTGGTC
 951 GGTCTAGGGG AATCGCGAAG ACCGAGGAGG GCGGCTCTCG CCTCCCTCCG
1001 TACACGGTCC GATCTCCGTT CCGTTTTCCC TTCCGCCCGT TGAGTCCGGA
1051 GTCCGGAACC GGTACCGGAG TCTTTGGGGG ACCCGCCACT CGAGTCGGTC
1101 GTGCAACAGA TCCATCGACC GCAGCCCCAT CGGCACTGGT CACTCCAACC
```

FIG.1A

```
1151 TTGGTTTGAG GCAGAACACC ACTTAGAGCA AGGTGTGGTG CCACAGGCTG
1201 AGCGGGCACC ACAACCTACA AGGCTATCAC TTCTACTCAG ACGCAAGGGT
1251 CCGCCACTAC TCGTTAGAGT CGTGGAAAGC CGGGAAGAGT AACAACCCAT
1301 CCATCGTCAC CGCTCCCTTC GGAGACCGAC ACTTGAAGAA CGGACCCAAC
1351 CCTACAAGTC CCGGGACCTA CGGGCACCCC TACAGTATCT GCTACGCCTA
1401 GCAGACCCAC AGACGTTTTG GTCCGTCGCT CACGCCCTAC TCCACTTTGA
1451 GGTAGAAGGG ACCACCGACA CAGGGACAGA AGAGGGGCAT CTACCGAAAC
1501 GTCCAACCTG TGACGTCCGA CGGTAGGAAC AACGGTAACC TCATGTACCG
1551 GTGGTCCGTC TCGTCCACTA TGTACACCGG CGTCGCCGGG TCCGCCGGGT
1601 GTTCGAGCCC GGCGTGTGAG AACAAAGCCT CGTGCGGGAG TATCGGTCTA
1651 CGACACTGGT CGGCGAGGTA CGTTTACCAT GTCAGGAGTA GTCCGCCCAA
1701 AAAGTGGAAG ACGTACATGG AGGCTTGGTG TAGGAGTCCT AAGAACGAAA
1751 AGAACTCCAC AAAGAAGAAC CAGAACGCCG TGTGCGGCCC GTGAGGTCCG
1801 TGTCCGAAGT GCAGCGAAAA CGAATGACCA CCACCCACGT CCTACCCAAA
1851 CCCACGAGCA CAGTCCGTGT GGCCGTCGGG GCGACGTGTG TCGTCCTAGG
1901 GCCAGTAGGG ACGGTTCCGA CCCACCTGTC CCGGTCACGG TAAGTTCAAG
1951 AAGTGCCCCT CGCGGCCTTG GGGTCCGCCC TATCTCCGCG CACGCGACTG
2001 CGACCACCTG GAGACACCAG GACCAGCTGA CTCCAACAAA ACCGGGCCAC
2051 ACCGCGAGG CAACCCCCGT GATCCCGAGG AACCCCCTTG AGGACCTCCG
2101 CCGCGTCCGA GGCACCCCGG CCACCGTCCA CGCCGGGTCT CGCGTCGAGG
2151 CCGCTTTCAC CGCGACCCCG CGTGTTGCTC GCGTGGGCCT CCAGGAGGCC
2201 CACCGTCGCC GCCGCCCCG CCTCCCCCGC GACCTCCGCG CCGACCGCGT
2251 TACCCTCGGA ACGCCGCGAC GCTCCGGTCC TACCGCAACC TCCGCCGCGC
2301 GCACGACAAC TGGTCGTCCG TGACGACTGT CCTCGTCCCG ACTGGGCTCG
2351 ACCGAGGGTG CCCGGTCCTA ACGCTGAACC CTTACCTCGG CTGTCACTCG
2401 CCCATTCGGT CCAGGTCCGC TGCCGCGTCC GCCGCCGCCG CCGCGCAGAC
2451 CGCCAAGTAG ACCCTGTACG ACAACTTCAT CTACTCCATC GTCTTCGGCT
2501 CGCTACTCTC CAGCTCGGTG CCCACGACGA AGAGCATGCG CAAGACCTAC
2551 CACTACGTCT ACAGGTACAG CATCCGGCAG GTGCGGGGCG GCAGCAAGAG
2601 GGTAAGGGTG TGCTACGGGA ACGGGCCGCG GCTGCTACCT AGCATCTTCA
2651 ACGCAGCGTG GCCGGCGTAC CATGGACACG AGTCCTCCCT CTCTCTACAG
2701 TTATGTCCGG GGGTTCTCCC TGGGAAGCTT CGGTCCTTCC CCTAGTCGCG
2751 TCTGTCCCTC TAAGTTCTGT ACCTCTGACC CGGAGGCTAT ACCGAGTCGT
2801 CCCCTTCCAC GAACGGTGGT TCGGACTGTT GTTCTAAGAT TAGGGTCTCT
2851 GGGCGCACCA CCTTCCTCTC TTAGCCAAGG GAGTCCGAAA CTAGACTGGA
2901 GGTTATTTAA TTATTTATTT TCGTTAATTT TAAAATTTTC CGTTCCCCCG
2951 ACCCTTTCTA CGACC
```

FIG.1B

SEQUENCE LISTING

<160> NUMBER OF SEQ ID NOS: 3

<210> SEQ ID NO 1
<211> LENGTH: 539
<212> TYPE: PRT
<213> ORGANISM: mammalian

<400> SEQUENCE: 1

```
Met Arg Pro Val Arg Arg Asn Phe Tyr Asp Pro Ser Ser Ala Pro Gly
 1               5                  10                  15

Lys Gly Ile Val Trp Glu Trp Glu Asn Asp Gly Gly Ala Trp Thr Ala
             20                  25                  30

Tyr Asp Met Asp Ile Cys Ile Thr Ile Gln Asn Ala Tyr Glu Lys Gln
             35                  40                  45

His Pro Trp Leu Asp Leu Ser Ser Leu Gly Phe Cys Tyr Leu Ile Tyr
     50                  55                  60

Phe Asn Ser Met Ser Gln Met Asn Arg Gln Thr Arg Arg Arg Arg Arg
 65                  70                  75                  80

Leu Arg Arg Arg Leu Asp Leu Ala Tyr Pro Leu Thr Val Gly Ser Ile
                 85                  90                  95

Pro Lys Ser Gln Ser Trp Pro Val Gly Ala Ser Ser Gly Gln Pro Cys
                100                 105                 110

Ser Cys Gln Gln Cys Leu Leu Val Asn Ser Thr Arg Ala Ala Ser Asn
            115                 120                 125

Ala Ile Leu Ala Ser Gln Arg Arg Lys Ala Pro Ile Ala Pro Ala Ala
        130                 135                 140

Pro Pro Ala Pro Pro Pro Pro Pro Leu Pro Pro Gly Gly Pro
145                 150                 155                 160

Pro Gly Ala Leu Val Val Arg Pro Ser Ala Thr Phe Ala Gly Ala Ala
                165                 170                 175

Leu Trp Ala Ala Pro Ala Thr Gly Pro Thr Glu Pro Ala Pro Pro Pro
            180                 185                 190

Gly Val Pro Pro Arg Ser Pro Ser Ala Pro Asn Gly Ala Pro Thr Pro
        195                 200                 205

Gly Gln Asn Asn Leu Ser Arg Pro Gly Pro Gln Arg Ser Thr Ser Val
    210                 215                 220

Ser Ala Arg Ala Ser Ile Pro Pro Gly Val Pro Ala Leu Pro Val Lys
225                 230                 235                 240

Asn Leu Asn Gly Thr Gly Pro Val His Pro Ala Leu Ala Gly Met Thr
                245                 250                 255

Gly Ile Leu Leu Cys Ala Ala Gly Leu Pro Val Cys Leu Thr Arg Ala
            260                 265                 270

Pro Lys Pro Ile Leu His Pro Pro Val Ser Lys Ser Asp Val Lys
        275                 280                 285

Pro Val Pro Gly Val Pro Gly Val Cys Arg Lys Thr Lys Lys His
    290                 295                 300

Leu Lys Lys Ser Lys Asn Pro Glu Asp Val Val Arg Arg Tyr Met Gln
305                 310                 315                 320

Lys Val Lys Asn Pro Pro Asp Glu Asp Cys Thr Ile Cys Met Glu Arg
                325                 330                 335
```

-continued

```
Leu Val Thr Ala Ser Gly Tyr Glu Gly Val Leu Arg Asn Lys Ser Val
                340                 345                 350
Arg Pro Glu Leu Val Gly Arg Leu Gly Arg Cys Gly His Met Tyr His
            355                 360                 365
Leu Leu Cys Leu Val Ala Met Tyr Ser Asn Gly Asn Lys Asp Gly Ser
        370                 375                 380
Leu Gln Cys Pro Thr Cys Lys Ala Ile Tyr Gly Glu Lys Thr Gly Thr
385                 390                 395                 400
Gln Pro Pro Gly Lys Met Glu Phe His Leu Ile Pro His Ser Leu Pro
                405                 410                 415
Gly Phe Ala Asp Thr Gln Thr Ile Arg Ile Val Tyr Asp Ile Pro Thr
            420                 425                 430
Gly Ile Gln Gly Pro Glu His Pro Asn Pro Gly Lys Lys Phe Thr Ala
        435                 440                 445
Arg Gly Phe Pro Arg His Cys Tyr Leu Pro Asn Asn Glu Lys Gly Arg
450                 455                 460
Lys Val Leu Arg Leu Leu Ile Thr Ala Trp Glu Arg Arg Leu Ile Phe
465                 470                 475                 480
Thr Ile Gly Thr Ser Asn Thr Thr Gly Glu Ser Asp Thr Val Val Trp
                485                 490                 495
Asn Glu Ile His His Lys Thr Glu Phe Gly Ser Asn Leu Thr Gly His
            500                 505                 510
Gly Tyr Pro Asp Ala Ser Tyr Leu Asp Asn Val Leu Ala Glu Leu Thr
        515                 520                 525
Ala Gln Gly Val Ser Glu Ala Met Ala Lys Ala
            530                 535

<210> SEQ ID NO 2
<211> LENGTH: 2965
<212> TYPE: DNA
<213> ORGANISM: mammalian

<400> SEQUENCE: 2
ccagcatctt tcccagcccc cttgcctttt aaaatttttaa ttgcttttat ttattaattt      60
attggaggtc agatcaaagc tgagggaac cgattctctc cttccaccac gcgggtctct      120
gggattagaa tcttgttgtc aggcttggtg gcaagcacct tcccctgctg agccatatcg      180
gaggcccagt ctccatgtct tgaatctccc tgtctgcgct gatccccttc ctggcttcga      240
agggtccctc ttgggggcct gtattgacat ctctctccct cctgagcaca ggtaccatgc      300
ggccggtgcg acgcaacttc tacgatccat cgtcggcgcc gggcaagggc atcgtgtggg      360
aatgggagaa cgacggcggg gcgtggacgg cctacgacat ggacatctgc atcaccatcc      420
agaacgcgta cgagaagcag cacccgtggc tcgacctctc atcgctcggc ttctgctacc      480
tcatctactt caacagcatg tcccagatga accgccagac gcgccgccgc cgccgcctgc      540
gccgtcgcct ggacctggct tacccgctca ctgtcggctc cattcccaag tcgcaatcct      600
ggcccgtggg agccagctcg ggtcagccct gctcctgtca gcagtgcctg ctggtcaaca      660
gcacgcgcgc cgcctccaac gccatcctgg cctcgcagcg ccgcaaggct cccattgcgc      720
cagccgcgcc tccagcgccc cctccgcccc gccgccgct gccacccgga ggacctccgg      780
gtgcgctcgt tgtgcgcccc agcgccactt cgccggagc tgcgctctgg gccgcacctg      840
ccaccggccc cacggagcct cgccgcctc caggagttcc cccaaggagc cctagtgccc      900
ccaacggagc gcccacaccg ggccaaaaca acctcagtcg accaggacca cagaggtcca      960
```

-continued

```
ccagcgtcag cgcacgcgcc tctatcccgc ctggggttcc ggcgctcccc gtgaagaact      1020
tgaatggcac tggccctgtc cacccagcct tggcagggat gaccgggatc ctgctgtgtg      1080
cagcggggct gccggtgtgc ctgacacgag cacccaaacc catcctgcac ccaccaccag      1140
taagcaaaag cgacgtgaag cctgtgcctg gagtgcccgg cgtgtgccgc aagaccaaga      1200
gagaaacacc tcaagaaaag caagaatcct gaggatgtgg ttcggaggta catgcagaag      1260
tgaaaaaccc gcctgatgag gactgtacca tttgcatgga gcggctggtc acagcatctg      1320
gctatgaggg cgtgctccga aacaagagtg tgcggcccga gcttgtgggc cgcctgggcc      1380
gctgcggcca catgtatcac ctgctctgcc tggtggccat gtactccaat ggcaacaagg      1440
atggcagcct gcagtgtcca acctgcaaag ccatctacgg ggagaagaca gggacacagc      1500
caccagggaa gatggagttt cacctcatcc cgcactcgct gcctggtttt gcagacaccc      1560
agacgatccg catcgtctat gacatcccca cgggcatcca gggccctgaa catcccaacc      1620
caggcaagaa gttcacagcc agaggcttcc ctcgccactg ctacctaccc aacaatgaga      1680
agggccgaaa ggtgctgaga ttgctcatca ccgcctggga acgcagactc atcttcacta      1740
tcggaacatc caacaccacg ggcgagtcgg acaccgtggt gtggaacgag attcaccaca      1800
agacggagtt tggttccaac ctcactggtc acggctaccc cgacgccagc tacctagaca      1860
acgtgctggc tgagctcacc gcccagggg tttctgaggc catggccaag gcctgaggcc      1920
tgagttgccc gccttccctt ttgccttgcc tctagcctgg cacatgcctc cctccgctct      1980
cggcgggagg agccagaagc gctaagggga tctggctggt ggctgtgggg ggggtgatgg      2040
gagtccacca ggccagctgg ctccaacctg tggcttccgg caagagcagc agagatagga      2100
ccaccagcaa gggcgacttc cctatggaaa acgatggcgc tttgcccttc acaccacaca      2160
caaacgcaca cgtgtcctgt tgcacgcacg cactcacgca cgtacaccac gtgcctctcc      2220
acttctccca gcttggggag aaagagacag aaaggccccc atgacatgtc ctgtggaaat      2280
acctgtgtct ccattacatc tgtataggct cgtccctttc ccaggacttg agtcaagcac      2340
gggatagtgg gggggactct gtaaggcttc aaggggtcgc tctgcccctg ggcctcaacc      2400
ccttaaccca cgtcagcgct gccacctgcc cactgagcac tgcaaagcca atgggtaga       2460 aaccccaggt tattaagtag cttttcgcag gccactgggg acgaggctat cttaactttg      2520
tgcttgtgtc tatctttccc gggaccctga cttcttcttc ttcctgtgtc catctcttga      2580
cctctgtcta tcccaggcaa agacatcgtc cttgcctctg taccggcttc tcccccacta      2640
aaccgctccg gacatttgag acccacttct ggcttcagga gcgaggggag gaggccttgt      2700
tcaggctata cacgcatcaa gctgagcagg cagcaaagcg ttaaacttct ccctgcttga      2760
aagtgggcgg tgggcggctg atcgtctcag gccaaccaga ggcccgttgc ccaggcaact      2820
caccagctcc gcctctgagg attggctgct gggatggaag tcagccaagc tttaaaggga      2880
cgccagcaat tgctcttttg gaaaaaaaaa aaaatctac cagtcccact gtgggtggag       2940
aaataaatgg tctttctcct taaaa                                            2965
```

<210> SEQ ID NO 3
<211> LENGTH: 2965
<212> TYPE: DNA
<213> ORGANISM: mammalian

<400> SEQUENCE: 3

```
ggtcgtagaa agggtcgggg gaacggaaaa ttttaaaatt aacgaaaata aataattaaa        60
taacctccag tctagtttcg gactcccttg gctaagagag gaaggtggtg cgcccagaga       120
```

-continued

```
ccctaatctt agaacaacag tccgaaccac cgttcgtgga agggacgac tcggtatagc     180 ctccgggtca gaggtacaga acttagaggg acagacgcga ctaggggaag gaccgaagct    240
tcccagggag aaccccggga cataactgta gagagaggga ggactcgtgt ccatggtacg    300
ccggccacgc tgcgttgaag atgctaggta gcagccgcgg cccgttcccg tagcacaccc    360
ttaccctctt gctgccgccc cgcacctgcc ggatgctgta cctgtagacg tagtggtagg    420
tcttgcgcat gctcttcgtc gtgggcaccg agctggagag tagcgagccg aagacgatgg    480
agtagatgaa gttgtcgtac aggtctact tggcggtctg cgcggcgcg gcggcggacg      540 cggcagcgga cctggaccga atgggcgagt gacagccgag gtaagggttc agcgttagga    600
ccgggcaccc tcggtcgagc ccagtcggga cgaggacagt cgtcacggac gaccagttgt    660
cgtgcgcgcg gcggaggttg cggtaggacc ggagcgtcgc ggcgttccga gggtaacgcg    720
gtcggcgcgg aggtcgcggg ggaggcgggg gcggcggcga cggtgggcct cctggaggcc    780
cacgcgagca acacgcgggg tcgcggtgaa agcggcctcg acgcgagacc cggcgtggac    840
ggtggccggg gtgcctcgga cgcggcggag gtcctcaagg gggttcctcg ggatcacggg    900
ggttgcctcg cgggtgtggc ccggttttgt tggagtcagc tggtcctggt gtctccaggt    960
ggtcgcagtc gcgtgcgcgg agatagggcg gaccccaagg ccgcgagggg cacttcttga   1020
acttaccgtg accgggacag gtgggtcgga accgtcccta ctggccctag gacgacacac   1080
gtcgccccga cggccacacg gactgtgctc gtgggtttgg gtaggacgtg ggtggtggtc   1140
attcgttttc gctgcacttc ggacacggac ctcacgggcc gcacacgcg ttctggttct    1200 ctctttgtgg agttcttttc gttcttagga ctcctacacc aagcctccat gtacgtcttc   1260 acttttggg cggactactc ctgacatggt aaacgtacct cgccgaccag tgtcgtagac    1320
cgatactccc gcacgaggct ttgttctcac acgccgggct cgaacacccg gcggacccgg   1380
cgacgccggt gtacatagtg gacgagacgg accaccggta catgaggtta ccgttgttcc   1440
taccgtcgga cgtcacaggt tggacgtttc ggtagatgcc cctcttctgt ccctgtgtcg   1500
gtggtccctt ctacctcaaa gtggagtagg gcgtgagcga cggaccaaaa cgtctgtggg   1560
tctgctaggc gtagcagata ctgtagggt gcccgtaggt cccgggactt gtaggttgg     1620 gtccgttctt caagtgtcgg tctccgaagg gagcggtgac gatggatggg ttgttactct   1680
tcccggcttt ccacgactct aacgagtagt ggcggaccct tgcgtctgag tagaagtgat   1740
agccttgtag gttgtggtgc ccgctcagcc tgtggcacca caccttgctc taagtggtgt   1800
tctgcctcaa accaaggttg gagtgaccag tgccgatggg gctgcggtcg atggatctgt   1860
tgcacgaccg actcgagtgg cgggtccccc aaagactccg gtaccggttc cggactccgg   1920
actcaacggg cggaagggaa aacggaacgg agatcggacc gtgtacggag ggaggcgaga   1980
gccgccctcc tcggtcttcg cgattcccct agaccgacca ccgacacccc cccactaccc   2040
ctcaggtggt ccggtcgacc gaggttggac accgaaggcc gttctcgtcg tctctatcct   2100
ggtggtcgtt cccgctgaag ggataccttt tgctaccgcg aaacgggaag tgtggtgtgt   2160
gtttgcgtgt gcacaggaca acgtgcgtgc gtgagtgcgt gcatgtggtg cacggagagg   2220
tgaagagggt cgaacccctc tttctctgtc tttccggggg tactgtacag gacaccttta   2280
tggacacaga ggtaatgtag acatatccga gcagggaaag ggtcctgaac tcagttcgtg   2340
ccctatcacc cccctgaga cattccgaag ttccccagcg agacgggac ccggagttgg    2400 ggaattgggt gcagtcgcga cggtggacgg gtgactcgtg acgtttcggt tacccatct    2460 ttggggtcca ataattcatc gaaaagcgtc cggtgacccc tgctccgata gaattgaaac   2520
```

```
acgaacacag atagaaaggg ccctgggact gaagaagaag aaggacacag gtagagaact    2580
ggagacagat agggtccgtt tctgtagcag gaacggagac atggccgaag aggggggtgat  2640 ttggcgaggc ctgtaaactc tgggtgaaga ccgaagtcct cgctcccctc ctccggaaca   2700
agtccgatat gtgcgtagtt cgactcgtcc gtcgtttcgc aatttgaaga gggacgaact   2760
ttcacccgcc acccgccgac tagcagagtc cggttggtct ccgggcaacg ggtccgttga   2820
gtggtcgagg cggagactcc taaccgacga ccctaccttc agtcggttcg aaatttccct   2880
gcggtcgtta acgagaaaac cttttttttt tttttagatg gtcagggtga cacccacctc   2940
tttatttacc agaaagagga atttt                                          2965
```

MAMMALIAN AND HUMAN FXI-T1

This application claims the benefit under 35 U.S.C. §119(e) of provisional Application No. 60/023,173 filed Aug. 5, 1996.

1. FIELD OF THE INVENTION

The present invention concerns the field of molecular genetics and medicine. Particularly, it concerns a gene, FXI-T1, whose mRNA levels are increased in fractionated X-irradiation induced leukemias and methods of using FXI-T1 to classify tissue samples for medical purposes. Specifically, the invention concerns the murine and human homologs of FXI-T1.

2. BACKGROUND OF THE INVENTION

The observation that fractionated X-irradiation (FX) causes a high incidence of leukemia in genetically susceptible mouse strains was first described by Kaplan and collaborators nearly 50 years ago. Kaplan, H. S., 1963, Nat'l. Cancer Inst. Monograph, 207–217. The presence of thymoma cells has been detected in greater than 90% of mice 4 months after FX-treatment. Muto, M., et al., 1987, Cancer Res. 47:3469–3472. The high incidence and fast onset of FX-induced leukemia suggests the involvement of epigenetic mechanisms in the disease process. Kaplan, H. S., 1963, Nat'l. Cancer Inst. Monograph, 207–217; Becker, Y., et al., 1993, In Vivo 7:281–284; Boniver, J., et al.,1981, Cancer Res. 41:390–392; Defresne, M. P., et al., 1986, J. Nat'l Cancer Inst. 77:1079–1085; Defresne, M. P., et al., 1986, Leukemia Res. 10:783–789; Gjerset, R. A., et al., 1992, Mol. Carcinog. 5:190–198; Haas, M., et al., 1986, EMBO J. 5:1775–1782; Muto, et al., 1985, J. Immunol. 134:2026–2031; Muto, M., et al., 1990, J. Immunol. 144:849–853; Sado, T., et al., 1991, Radiation Res. 32:168–180.

In the past decade, several laboratories have investigated the cellular interactions of FX-induced leukemogenesis. The leukemogenic process induced by FX-treatment can be divided into two stages. Defresne, M. P., et al., 1986, Leukemia Res. 10:783–789. In the first stage, radiation injury causes thymic atrophy and depletion of prothymocytes and other cell populations from the bone marrow. Muto, M., et al., 1987, Cancer Res. 47:3469–3472; Becker, Y., et al., 1993, In Vivo 7:281–284; Muto, et al., 1985, J. Immunol. 134:2026–2031. Tumor induction by cycles of tissue injury and cell regeneration can explain initial observations that an approximate threshold dose of 200 rad is required, apparently to cause sufficient tissue damage. Defresne, M. P., et al., 1986, J. Nat'l Cancer Inst. 77:1079–1085. Greater tumor incidence occurs when radiation is split among 4 doses spaced several days apart. Kaplan, H. S., 1963, Nat'l. Cancer Inst. Monograph, 207–217. Thymic involvement in the disease process is indicated by observations that thymectomy, before or shortly after FX-treatment, prevents tumor induction and that genetic susceptibility to FX is transmitted with thymus grafts. Id. Tumors developing in untreated thymus grafts, after transplantation into thymectomized FX-treated mice, have been immunogenetically identified as donor-derived indicating that FX-treatment of the host can indirectly cause transformation of untreated donor thymus cells. Id. Noting that syngeneic thymus grafts initially become necrotic before they establish in the recipient, Kaplan suggested that transplantation may mimic FX-damage. He postulated that the manner of tissue damage could be nonspecific and that the circumstances of thymic regeneration would determine the leukemogenic outcome; an untreated thymus transplanted into a FX-treated host develops lymphoma but, when transplanted into an untreated host, the untreated thymus regenerates normally.

Stage 1 lymphomagenesis lasts 1–2 months after FX-treatment during which time prethymoma cells first arise in the thymus from surviving cells. Kaplan, H. S., 1963, Nat'l. Cancer Inst. Monograph, 207–217; Muto, M., et al., 1987, Cancer Res. 47:3469–3472; Boniver, J., et al.,1981, Cancer Res. 41:390–392. Stage 1 can be reversed by transfer of nonirradiated bone marrow cells to FX-treated recipients. Shielding of bone marrow during FX-treatment also abrogates tumor development. Kaplan, H. S., 1963, Nat'l. Cancer Inst. Monograph, 207–217. Bone marrow cells do not prevent induction of prethymoma cells but apparently inhibit their progression by restoring cell populations to the damaged thymus. Muto, M., et al., 1987, Cancer Res. 47:3469–3472; Becker, Y., et al., 1993, In Vivo 7:281–284; Boniver, J., et al.,1981, Cancer Res. 41:390–392; Defresne, M. P., et al., 1986, J. Nat'l Cancer Inst. 77:1079–1085. In the 2nd stage of leukemogenesis, occurring from 2 months post FX-treatment onward, the radiation-induced damage becomes irreversible and prethymoma cells progress to overt tumors; cells from this stage can grow autonomously outside the thymus. Muto, M., et al., 1987, Cancer Res. 47:3469–3472.

The thymic microenvironment plays a role in prethymoma development. Becker, Y., et al., 1993, In Vivo 7:281–284; Defresne, M. P., et al., 1986, J. Nat'l Cancer Inst. 77:1079–1085; Defresne, M. P., et al., 1986, Leukemia Res. 10:783–789. FX-treatment has been shown to affect two thymic cell populations involved with T-cell maturation, dendritic cells and thymus epithelial nurse cells. Id. The diminished supply of healthy prothymocytes and dendritic cells from the bone marrow to the atrophied thymus of FX-treated mice appears to be a key factor for leukemia development. Kaplan, H. S., 1963, Nat'l. Cancer Inst. Monograph, 207–217; Becker, Y., et al., 1993, In Vivo 7:281–284; Boniver, J., et al.,1981, Cancer Res. 41:390–392; Sado, T., et al., 1991, Radiation Res. 32:168–180. It has been shown that although FX-treated bone marrow does contain a small number of T-cell precursors, capable of migration to the thymus and expression of Thy-1 antigen, they are unable to proliferate and differentiate into functional T cells. Muto, et al., 1985, J. Immunol. 134:2026–2031. Impaired thymic regeneration eventually results in differentiation arrest of immature prothymocytes. Kaplan, H. S., 1963, Nat'l. Cancer Inst. Monograph, 207–217; Boniver, J., et al.,1981, Cancer Res. 41:390–392; Sado, T., et al., 1991, Radiation Res. 32:168–180. FX-induced thymomas represent several early stages of T-cell development as evidenced by cell surface antigens and T-cell receptor gene rearrangements; the ability to detect T-cell receptor gene rearrangements within a thymoma cell population implies a clonal outgrowth of individual prethymoma cells. Gjerset, R. A., et al., 1992, Mol. Carcinog. 5:190–198; Muto, M., et al., 1990, J. Immunol. 144:849–853; Amari, N. M., & Meruelo, D., 1987, Mol. Cell. Biol. 7:4159–4168; Crispe, N., and Bevan, M. J., 1987, J. Exp. Med. 138:2013–2018; Diamond, L. E., et al. 1988, Immunogenetics 28:71–80; Shimizu, T., et al., 1993, Leukemia Res. 17:959–965.

FX-induced injury has been proposed to cause leukemia by altering the balance between the rates of differentiation and pre-T cell renewal in the thymus. Gjerset, R. A., et al., 1992, Mol. Carcinog. 5:190–198. To identify mRNA transcripts associated with FX-induced thymomas a cDNA library was constructed from FX-induced thymoma mRNA and differentially screened in an attempt to isolate biologically significant cDNA transcripts. A novel cDNA clone, FX-induced transcript 1 (FXI-T1), is described. For the purposes of this specification, the term "isolate" means to remove from the cell, free of the majority of the genomic DNA and mRNA normally found in a cell. Increased FXI-T1 mRNA expression appears to be associated with FX-induced thymomas.

The inventors have transmitted to Genbank the mRNA sequence of FXI-T1, which sequence was published on Jun. 29, 1996 and given Genbank accession number U38252.

3. SUMMARY OF THE INVENTION

The invention embraces nucleic acids encoding a FXI-T1 gene. In further embodiments, the invention concerns a plasmid comprising a FXI-T1 encoding portion operably linked to heterologous promoters so that FXI-T1 can be expressed in eukaryotic cells, other than leukemic cells, and bacteria.

The invention additionally provides methods of use in the areas of providing medical diagnoses and prognoses. The invention provides a method of classifying a human tissue sample by determining the level of FXI-T1 expression.

4. BRIEF DESCRIPTION OF THE FIGURES

FIG. 1. FIG. 1 shows derived amino acid sequence of FXI-T1 (SEQ ID NO:1) and the nucleic acid sequences of the FXI-T1 mRNA (SEQ ID NO:2) and the complement thereof (SEQ ID NO:3).

FIG. 2. FIG. 2 shows the autoradiograph of a Southern blot using murine FXI-T1 as a probe against EcoRI digested genomic DNA from mouse (M), hamster (H), rabbit (R), bovine (B), monkey (Mo), human (Hu), and chicken (C) tissue samples.

Figure 3:
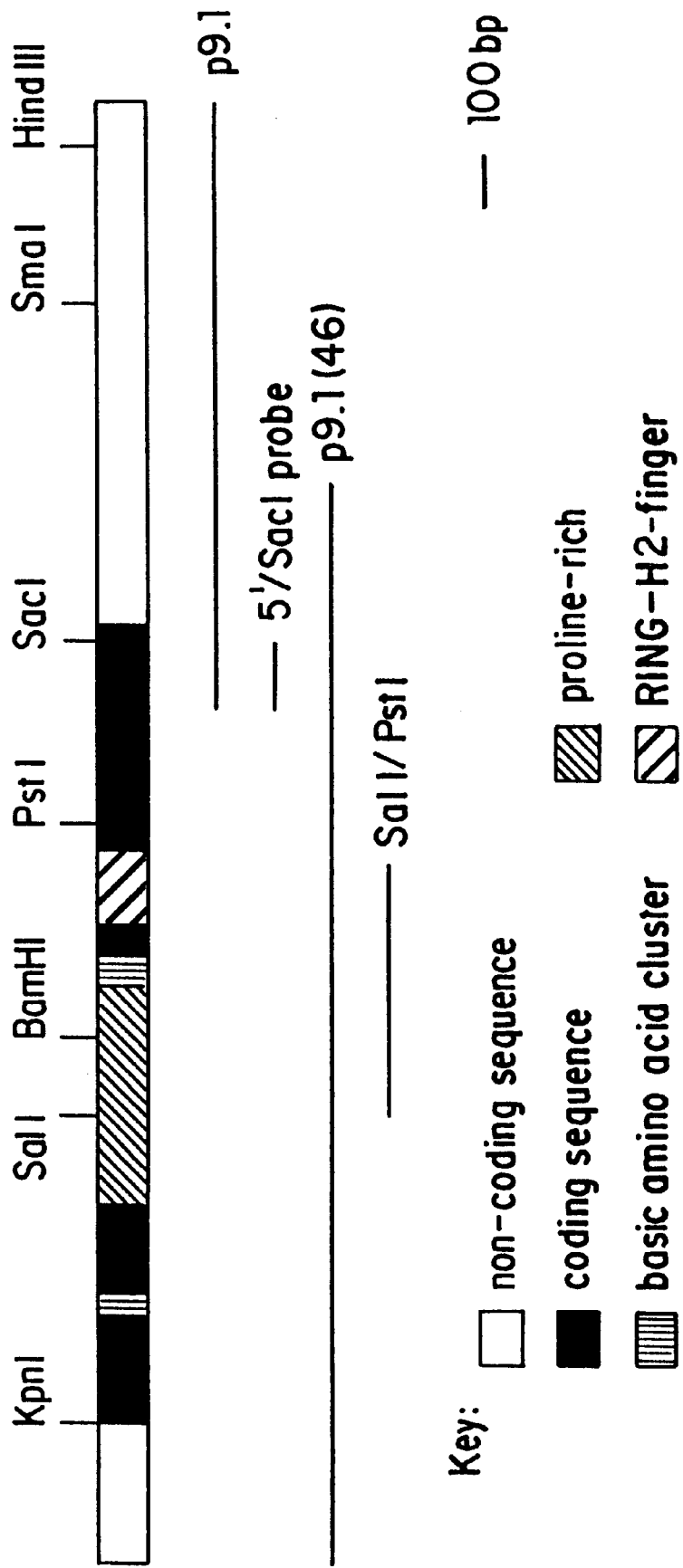

FIG. 3. FIG. 3 shows a schematic diagram of the FXI-T1 cDNA. A partial restriction endonuclease map and positions of several fragments are shown.

5. DETAILED DESCRIPTION OF THE INVENTION 5.1 Isolation of FXI-T1 cDNA

To isolate cDNA clones associated with FX-induced leukemogenesis, a thymoma cDNA library was differentially screened using, for positive selection, a $^{32}$P-FX induced-thymoma cDNA probe subtracted with normal thymus cDNA sequences. $^{32}$P-cDNA probes, prepared from serum-starved and serum-stimulated cells, were used to detect and eliminate clones that potentially reflect general differences in proliferation rates between normal and tumor cells. The subtractive probe was prepared by a DNA:DNA phenol reassociation technique, which greatly enhances the rate of hybridization while avoiding problems inherent with RNA:DNA hybridizations due to the relative instability of RNA and the difficulty of obtaining sufficient quantities of poly(A+) RNA to drive subtraction. Travis, G. H., et al., 1990, In A. A. Boulton, G. B. Baker, A. T. Campagnoni (eds), Neuromethods, vol 16, pp. 49–77. Clifton, N.J., Humana Press; Kohne, D. E., et al., 1977, Biochemistry 16:5329–5341. Clones isolated by this protocol were analyzed for their ability to preferentially hybridize with FX-induced thymoma RNA compared with normal thymus RNA in northern blots and by sequence analysis. A clone was selected for more extensive analysis as it appeared to be a novel cDNA transcript that showed strong differential mRNA expression in FX-induced thymomas compared with normal thymus tissue. A full-length cDNA sequence was isolated using a probe, prepared from the 5' end of the previously selected clone, to rescreen a random hexanucleotide-primed FX-induced murine thymoma cDNA library derived from the C57BL/6 mouse strain. The resulting FX-induced transcript 1 (FXI-T1) sequence is a composite of two cDNA clones from this second screening that overlap by 400 bp. Fragments generated from non-overlapping regions of each clone yield identical patterns when used as probes in northern blot hybridizations (not shown) indicating that they are derived from the same mRNA transcript. Northern hybridization of a Sal I/Pst I fragment of the clone to fractionated X-irradiation induce thymoma RNA samples results in a band of approximately 4 kb along with multiple smaller bands and a broad band of approximately 2 kb in some samples.

The present invention encompasses mammalian homologs of FXI-T1. Nucleic acids encoding FXI-T1 from any mammalian species can be identified and isolated by techniques, routine to those skilled in the art, using the sequence information of FIG. 1 and/or the FXI-T1 cDNA clone. Such routine techniques include use of the FXI-T1 cDNA or fragments thereof to probe cDNA and genomic libraries from other mammalian species and use of the sequence data to construct primers for PCR amplification of fragments of mammalian FXI-T1 cDNA.

The invention includes nucleic acid molecules which hybridize to the FXI-T1 sequence in FIG. 1 under highly stringent conditions, e.g., hybridization to filter-bound DNA in 0.5 M NaHPO$_4$, 7% sodium dodecyl sulfate (SDS), 1 mM EDTA at 65° C, and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) and encodes a gene product functionally equivalent to a gene product encoded by sequences contained within FIG. 1; and/or any DNA sequence that hybridizes to the complement of the coding sequences disclosed herein, (as shown in FIG. 1) or contained within the coding region of the gene to which DNA sequences disclosed herein (as shown in FIG. 1) or under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of a cardiovascular disease-causing allele, may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

The invention includes fragments of any of the DNA sequences disclosed herein.

In addition to the gene sequences described above, homologues of such sequences, as may, for example be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

FIG. 2 shows that a Southern blot hybridization to the digested genomic DNA of several mammalian and one avian species revealed signals in all DNA samples indicating a conservation of FXI-T1 sequences. The low number of hybridization bands observed in the Eco RI digests, as well as several other restriction endonuclease digests (not shown), suggests FXI-T1 to be transcribed from a single or low-copy gene. Mammalian homologs of murine FXI-T1 (muFXI-T1) are termed an maFXI-T1 can be identified by sequence identity of greater that 70% and preferably greater than 90% compared to muFXI-T1.

The present invention also encompasses expression vectors containing FXI-T1 and the production of FXI-T1 protein in host cells using these vectors. One skilled in the art will know to select an appropriate promoter and host cell to produce FXI-T1 polypeptide.

5.2 The use of FXI-T1 Nucleotide Sequence to Predict Fractionated x Irradiation Induced Leukemia.

To ascertain the specificity of FXI-T1 expression, total RNA was examined in murine cell lines established from FXI-induced thymomas, thymomas induced by radiation leukemia virus, and cell lines generated from tumors induced by other mechanisms. All FXI-induced thymoma cell lines expressed the 4 kb transcript. A cell line derived from a chemically induced thymoma also showed an overabundance of FXI-T1 transcripts with predominance of the 2 kb species. Two non-FX-treated thymoma derived cell lines did not express FXI-T1. FXI-T1 transcripts were also absent from a fibrosarcoma cell line.

Preliminary evidence indicates that increased levels of FXI-T1 transcripts are observed at 2 months after FX treatment, prior to the appearance of overt tumors. The appearance of increased FXI-T1 transcripts at a relatively early stage of tumor progression is consistent with the finding of increased FXI-T1 RNA in all FX-induced thymomas. Only two other phenotypic markers have thus far been associated with all in vivo C57BL/6 FX-induced thymomas: J11d, an antigen occurring on cortical thymic T-cells, and TL-2, a T-cell tumor antigen. Muto, M., et al., 1990, J. Immunol. 144:849–853. Up regulation of FXI-T1 mRNA expression does not correlate with a general increase of the cellular proliferative rate; FXI-T1 mRNA levels were not induced in serum starved NIH3T3 cells that were subsequently stimulated with 20% fetal calf serum.

Total RNA was extracted from various normal mouse organs to examine the tissue distribution of FXI-T1. It was observed that FXI-T1 mRNA expression is not limited to the thymus or the hematopoietic system but was found to be expressed in brain, lung, skeletal muscle, spleen, thymus, testis and ovary tissues. Brain and skeletal muscle contain the highest levels of FXI-T1 transcripts. Little or no expression of FXI-T1 was observed in heart, kidney, liver or uterus tissue.

In one embodiment, the invention consists of classifying a tissue sample of a patient who has been exposed to fractionated X irradiation by assaying for increases of FXI-T1 transcripts in the thymus as a predictor for subsequent development of a leukemia, which is homologous to FX induced.

5.2 The Use of FXI-T1 Nucleotide Sequence to Diagnose Fractionated X-irradiation Induced Leukemia.

In another embodiment, the invention consists of classifying a tissue sample of a patient who has presented with an undefined leukemia by determining the level of FXI-T1 transcripts in the sample as a diagnostic for X-irradiation or chemically induced leukemia.

5.3 FXI-T1 Homologs in Other Species.

The invention further encompasses homologs of FXI-T1 in other species. Genomic DNA from the mouse, hamster, rabbit, bovine, monkey, human, and chicken was digested with EcoRI and fractionated in agarose gels by standard protocols. A Southern hybridization was performed using murine FXI-T1 as a probe. Hybridization signals appeared in all DNA samples, indicating a conservation of FXI-T1 sequences.

5.6 ADDITIONAL MODIFICATIONS OF FXI-T1 GENE PRODUCTS

In addition, FXI-T1 gene products may include proteins that represent functionally equivalent gene products. Such an equivalent FXI-T1 gene product may contain deletions, including internal deletions, additions, including additions yielding fusion proteins, or substitutions of amino acid residues within and/or adjacent to the amino acid sequence encoded by the FXI-T1 gene sequences described, above, but that result in a "silent" change, in that the change produces a functionally equivalent FXI-T1 gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

5.6 EXPRESSION OF FXI-T1 GENE PRODUCTS

Alternatively, where alteration of function is desired, deletion or non-conservative alterations can be engineered to produce altered FXI-T1 gene products. Such alterations can, for example, alter one or more of the biological functions of the FXI-T1 gene product. Further, such alterations can be selected so as to generate FXI-T1 gene products that are better suited for expression, scale up, etc. in the host cells chosen. For example, cysteine residues can be deleted or substituted with another amino acid residue in order to eliminate disulfide bridges.

The FXI-T1 gene products, peptide fragments thereof and fusion proteins thereof, may be produced by recombinant DNA technology using techniques well known in the art. Thus, methods for preparing the FXI-T1 gene polypeptides, peptides, fusion peptide and fusion polypeptides of the invention by expressing nucleic acid containing FXI-T1 gene sequences are described herein. Methods that are well known to those skilled in the art can be used to construct expression vectors containing FXI-T1 gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding FXI-T1 gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the FXI-T1 gene coding sequences of the invention. Such host-expression systems represent vehicles by which the coding sequences of interest may be produced and subsequently purified, but also represent cells that may, when transformed or transfected with the appropriate nucleotide coding sequences, exhibit the FXI-T1 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing FXI-T1 gene product coding sequences; yeast (e.g., *Saccharomyces, Pichia*) transformed with recombinant yeast expression vectors containing the FXI-T1 gene product coding sequences; insect cell systems infected with recombinant virus expression vectors (e.g., baculovirus) containing the FXI-T1 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing FXI-T1 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the FXI-T1 gene product being expressed. For example, when a large quantity of such a protein is to be produced, for the generation of pharmaceutical compositions of FXI-T1 protein or for raising antibodies to FXI-T1 protein, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the FXI-T1 gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhedrosis virus (AcNPV) is used as a vector to express foreign genes. The virus grows in *Spodoptera frugiperda* cells. The FXI-T1 gene coding sequence may be cloned individually into non-essential regions (for example the polyhedrin gene) of the virus and placed under control of an AcNPV promoter (for example the polyhedrin promoter).

Successful insertion of FXI-T1 gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the FXI-T1 gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing FXI-T1 gene product in infected hosts. (e.g., See Logan and Shenk, 1984, Proc. Natl. Acad. Sci. USA 81, 3655–3659). Specific initiation signals may also be required for efficient translation of inserted FXI-T1 gene product coding sequences. These signals include the ATG initiation codon and adjacent sequences. In cases where an entire FXI-T1 gene, including its own initiation codon and adjacent sequences, is inserted into the appropriate expression vector, no additional translational control signals may be needed. However, in cases where only a portion of the FXI-T1 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, CoS, MDCK, 293, 3T3, and WI38.

For long-term, high-yield production of recombinant proteins, stable expression is preferred. For example, cell lines that stably express the FXI-T1 gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the FXI-T1 gene product. Such engineered cell lines may be particularly useful in screening and evaluation of compounds that affect the endogenous activity of the FXI-T1 gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

The FXI-T1 gene products can also be expressed in transgenic animals. Animals of any species, including, but not limited to, mice, rats, rabbits, guinea pigs, pigs, micropigs, goats, sheep, and non-human primates, e.g., baboons, monkeys, and chimpanzees may be used to generate FXI-T1 transgenic animals. The term "transgenic," as used herein, refers to animals expressing FXI-T1 gene sequences from a different species (e.g., mice expressing human FXI-T1 sequences), as well as animals that have been genetically engineered to overexpress endogenous (i.e., same species) FXI-T1 sequences or animals that have been genetically engineered to no longer express endogenous FXI-T1 gene sequences (i.e., "knock-out" animals), and their progeny.

Any technique known in the art may be used to introduce an FXI-T1 gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229)

Any technique known in the art may be used to produce transgenic animal clones containing an FXI-T1 transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry an FXI-T1 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the FXI-T1 gene transgene be integrated into the chromosomal site of the endogenous FXI-T1 gene, gene targeting is preferred. Briefly, when such a technique is to be utilized, vectors containing some nucleotide sequences homologous to the endogenous FXI-T1 gene are designed for the purpose of integrating, via homologous recombination with chromosomal sequences, into and disrupting the function of the nucleotide sequence of the endogenous FXI-T1 gene. The transgene may also be selectively introduced into a particular cell type, thus inactivating the endogenous FXI-T1 gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant FXI-T1 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of FXI-T1 gene-expressing tissue, may also be evaluated immunocytochemically using antibodies specific for the FXI-T1 transgene product.

5.7 ANTIBODIES TO FXI-T1 GENE PRODUCTS

Described herein are methods for the production of antibodies capable of specifically recognizing one or more FXI-T1 gene product epitopes or epitopes of conserved variants or peptide fragments of the FXI-T1 gene products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a FXI-T1 gene product in an biological sample and may, therefore, be utilized as part of a diagnostic or prognostic technique whereby patients may be tested for abnormal levels of FXI-T1 gene products, and/or for the presence of abnormal forms of such gene products. Such antibodies may also be utilized in conjunction with, for example, compound screening schemes, as described, below, for the evaluation of the effect of test compounds on FXI-T1 gene product levels and/or activity. Additionally, such antibodies can be used in conjunction with the gene therapy techniques described, below, for example, evaluate the normal and/or engineered FXI-T1-expressing cells prior to their introduction into the patient.

Anti-FXI-T1 gene product antibodies may additionally be used as a method for the inhibition of abnormal FXI-T1 gene product activity. Thus, such antibodies may, therefore, be utilized as part of treatment methods for an FXI-T1 disorder.

For the production of antibodies against a FXI-T1 gene product, various host animals may be immunized by injection with a FXI-T1 gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a FXI-T1 gene product, or an antigenic functional derivative thereof. For the production of polyclonal antibodies, host animals such as those described above, may be immunized by injection with FXI-T1 gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobuin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against FXI-T1 gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science, 246, 1275–1281) to allow rapid and easy identification of monoclonal Fab fragments with the desired specificity.

5.8 USES OF FXI-T1 GENE SEQUENCES, GENE PRODUCTS, AND ANTIBODIES

Described herein are various applications of FXI-T1 gene sequences, FXI-T1 gene products, including peptide fragments and fusion proteins thereof, and of antibodies directed against FXI-T1 gene products and peptide fragments thereof. Such applications include, for example, prognostic and diagnostic evaluation of a FXI-T1 disorder and the identification of subjects with a predisposition to such disorders, as described, below. Additionally, such applications include methods for the treatment of a FXI-T1 disorder, as described, below, and for the identification of compounds that modulate the expression of the FXI-T1 gene and/or the synthesis or activity of the FXI-T1 gene product, as described below. Such compounds can include, for example, other cellular products that are involved in mood regulation and in FXI-T1 disorders. These compounds can be used, for example, in the amelioration of FXI-T1 disorders.

5.9 DIAGNOSIS OF ABNORMALITIES ASSOCIATED WITH FXI-T1

A variety of methods can be employed for the diagnostic and prognostic evaluation of FXI-T1 disorders and for the identification of subjects having a predisposition to such disorders.

Such methods may, for example, utilize reagents such as the FXI-T1 gene nucleotide sequences described above, and antibodies directed against FXI-T1 gene products, including peptide fragments thereof, as described, above. Specifically, such reagents may be used, for example, for:

(1) the detection of the presence of FXI-T1 gene mutations, or the detection of either over- or under-expression of FXI-T1 gene mRNA relative to the state of a FXI-T1 disorder;

(2) the detection of either an over- or an under-abundance of FXI-T1 gene product relative to the unaffected state; and (3) the detection of an aberrant level of FXI-T1 gene product activity relative to the unaffected state.

FXI-T1 gene nucleotide sequences can, for example, be used to diagnose an FXI-T1 disorder for example, the techniques for FXI-T1 mutation detection described above.

The methods described herein may be performed, for example, by utilizing pre-packaged diagnostic kits comprising at least one specific FXI-T1 gene nucleic acid or anti-FXI-T1 gene antibody reagent described herein, which may be conveniently used, e.g., in clinical settings, to diagnose patients exhibiting abnormalities of a FXI-T1 disorder.

For the detection of FXI-T1 mutations, any nucleated cell can be used as a starting source for genomic nucleic acid. For the detection of FXI-T1 gene expression or FXI-T1 gene products, any cell type or tissue in which the FXI-T1 gene is expressed may be utilized.

Nucleic acid-based detection techniques are described, below. Peptide detection techniques are described, below.

5.10 DETECTION OF FXI-T1 NUCLEIC ACID MOLECULES

A variety of methods can be employed to screen for the presence of FXI-T1 mutations and to detect and/or assay levels of FXI-T1 nucleic acid sequences.

Mutations within the FXI-T1 gene can be detected by utilizing a number of techniques. Nucleic acid from any nucleated cell can be used as the starting point for such assay techniques, and may be isolated according to standard nucleic acid preparation procedures that are well known to those of skill in the art.

FXI-T1 nucleic acid sequences may be used in hybridization or amplification assays of biological samples to detect abnormalities involving FXI-T1 gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of FXI-T1 gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described below, under conditions favorable for the specific annealing of these reagents to their complementary sequences within the FXI-T1 gene. Preferably, the lengths of these nucleic acid reagents are at least 15 to 30 nucleotides. After incubation, all non-annealed nucleic acids are removed from the nucleic acid:FXI-T1 molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled FXI-T1 nucleic acid reagents is accomplished using standard techniques well-known to those in the art. The FXI-T1 gene sequences to which the nucleic acid reagents have annealed can be compared to the annealing pattern expected from a normal FXI-T1 gene sequence in order to determine whether a FXI-T1 gene mutation is present.

Alternative diagnostic methods for the detection of FXI-T1 gene specific nucleic acid molecules, in patient samples or other appropriate cell sources, may involve their amplification, e.g., by PCR (the experimental embodiment set forth in Mullis, 1987, U.S. Pat. No. 4,683,202), followed by the detection of the amplified molecules using techniques well known to those of skill in the art. The resulting amplified sequences can be compared to those that would be expected if the nucleic acid being amplified contained only normal copies of the FXI-T1 gene in order to determine whether a FXI-T1 gene mutation exists.

Additionally, well-known genotyping techniques can be performed to identify individuals carrying FXI-T1 gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms, which can be utilized for the identification of FXI-T1 gene mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the FXI-T1 gene, and the diagnosis of diseases and disorders related to FXI-T1 mutations.

Also, Caskey et al. (U.S. Pat. No. 5,364,759) describe a DNA profiling assay for detecting short tri and tetra nucleotide repeat sequences. The process includes extracting the DNA of interest, such as the FXI-T1 gene, amplifying the extracted DNA, and labelling the repeat sequences to form a genotypic map of the individual's DNA.

The level of FXI-T1 gene expression can also be assayed. For example, RNA from a cell type or tissue known, or suspected, to express the FXI-T1 gene, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the FXI-T1 gene. Such analyses may reveal both quantitative and qualitative aspects of the expression pattern of the FXI-T1 gene, including activation or inactivation of FXI-T1 gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the FXI-T1 gene nucleic acid reagents described above. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such FXI-T1 gene expression assays "in situ", i.e., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the FXI-T1 gene.

5.11 DETECTION OF FXI-T1 GENE PRODUCTS

Antibodies directed against unimpaired or mutant FXI-T1 gene products or conserved variants or peptide fragments thereof, which are discussed, above, may also be used as diagnostics and prognostics for a FXI-T1 disorder. Such methods may be used to detect abnormalities in the level of FXI-T1 gene product synthesis or expression, or abnormalities in the structure, temporal expression, and/or physical location of FXI-T1 gene product. The antibodies and immunoassay methods described below have, for example, important in vitro applications in assessing the efficacy of treatments for FXI-T1 disorders. Antibodies, or fragments of antibodies, such as those described below, may be used to screen potentially therapeutic compounds in vitro to determine their effects on FXI-T1 gene expression and FXI-T1 peptide production. The compounds that have beneficial effects on an FXI-T1 disorder can be identified, and a therapeutically effective dose determined.

In vitro immunoassays may also be used, for example, to assess the efficacy of cell-based gene therapy for an FXI-T1 disorder. Antibodies directed against FXI-T1 peptides may be used in vitro to determine, for example, the level of FXI-T1 gene expression achieved in cells genetically engineered to produce FXI-T1 peptides. In the case of intracellular FXI-T1 gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the FXI-T1 gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the FXI-T1 gene.

Preferred diagnostic methods for the detection of FXI-T1 gene products or conserved variants or peptide fragments thereof, may involve, for example, immunoassays wherein the FXI-T1 gene products or conserved variants or peptide fragments are detected by their interaction with an anti-FXI-T1 gene product-specific antibody.

For example, antibodies, or fragments of antibodies, such as those described, above, useful in the present invention may be used to quantitatively or qualitatively detect the presence of FXI-T1 gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for FXI-T1 gene products that are expressed on the cell surface.

The antibodies (or fragments thereof) useful in the present invention may, additionally, be employed histologically, as in immunofluorescence or immunoelectron microscopy, for in situ detection of FXI-T1 gene products or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the FXI-T1 gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for FXI-T1 gene products or conserved variants or peptide fragments thereof will typically comprise incubating a sample, such as a biological fluid, a tissue extract, freshly harvested cells, or lysates of cells, that have been incubated in cell culture, in the presence of a detectably labeled antibody capable of identifying FXI-T1 gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled FXI-T1 gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-FXI-T1 gene product antibody may be determined according to well known methods. Those skilled in the art will be able to determine operative and optimal assay conditions for each determination by employing routine experimentation.

One of the ways in which the FXI-T1 gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect FXI-T1 gene peptides through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.12 SCREENING ASSAYS FOR COMPOUNDS THAT MODULATE FXI-T1 GENE ACTIVITY

The following assays are designed to identify compounds that bind to a FXI-T1 gene product, intracellular proteins or portions of proteins that interact with a FXI-T1 gene product, compounds that interfere with the interaction of a FXI-T1 gene product with intracellular proteins and compounds that modulate the activity of FXI-T1 gene (i.e., modulate the level of FXI-T1 gene expression and/or modulate the level of FXI-T1 gene product activity). Assays may additionally be utilized that identify compounds that bind to FXI-T1 gene regulatory sequences (e.g., promoter sequences; see e.g., Platt, 1994, J. Biol. Chem. 269, 28558–28562), and that may modulate the level of FXI-T1 gene expression. Compounds may include, but are not limited to, small organic molecules, such as ones that are able to cross the blood-brain barrier, gain entry into an appropriate cell and affect expression of the FXI-T1 gene or some other gene involved in a FXI-T1 regulatory pathway, or intracellular proteins.

Methods for the identification of such intracellular proteins are described, below. Such intracellular proteins may be involved in the control and/or regulation of mood. Further, among these compounds are compounds that affect the level of FXI-T1 gene expression and/or FXI-T1 gene product activity and that can be used in the therapeutic treatment of FXI-T1 disorders as described, below.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L- configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Compounds identified via assays such as those described herein may be useful, for example, in elaborating the biological function of the FXI-T1 gene product, and for ameliorating FXI-T1 disorders. Assays for testing the effectiveness of compounds, identified by, for example, techniques are discussed, below.

5.13 IN VITRO SCREENING ASSAYS FOR COMPOUND THAT BIND TO THE FXI-T1 GENE PRODUCT

In vitro systems may be designed to identify compounds capable of binding the FXI-T1 gene products of the invention. Compounds identified may be useful, for example, in modulating the activity of unimpaired and/or mutant FXI-T1 gene products, may be useful in elaborating the biological function of the FXI-T1 gene product, may be utilized in screens for identifying compounds that disrupt normal FXI-T1 gene product interactions, or may in themselves disrupt such interactions.

The principle of the assays used to identify compounds that bind to the FXI-T1 gene product involves preparing a reaction mixture of the FXI-T1 gene product and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring FXI-T1 gene product or the test substance onto a solid phase and detecting FXI-T1 gene product/test compound complexes anchored on the solid phase at the end of the reaction. In one embodiment of such a method, the FXI-T1 gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for FXI-T1 gene product or the test compound to anchor any complexes formed in solution, and a labeled antibody specific for the other component of the possible complex to detect anchored complexes.

6.14 ASSAYS FOR INTRACELLULAR PROTEINS THAT INTERACT WITH FXI-T1 GENE PRODUCTS

Any method suitable for detecting protein-protein interactions may be employed for identifying FXI-T1 protein-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with FXI-T1 gene products. Once isolated, such a protein can be identified and can be used in conjunction with standard techniques, to identify proteins it interacts with. For example, at least a portion of the amino acid sequence of a protein that interacts with the FXI-T1 gene product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode the a protein which interacts with an FXI-T1 protein. These methods include, for example, probing expression libraries with labeled FXI-T1 protein, using FXI-T1 protein in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the FXI-T1 gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, FXI-T1 gene products may be used as the bait gene product. Total genomic or cDNA sequences are fused to the DNA encoding an activation domain. This library and a plasmid encoding a hybrid of a bait FXI-T1 gene product fused to the DNA-binding domain are co-transformed into a yeast reporter strain, and the resulting transformants are screened for those that express the reporter gene. For example, and not by way of limitation, a bait FXI-T1 gene sequence, such as the open reading frame of the FXI-T1 gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait FXI-T1 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait FXI-T1 gene-GAL4 fusion plasmid into a yeast strain that contains a lacZ gene driven by a promoter that contains GAL4 activation sequence. A cDNA encoded protein, fused to GAL4 transcriptional activation domain, that interacts with bait FXI-T1 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait FXI-T1 gene-interacting protein using techniques routinely practiced in the art.

5.15 ASSAYS FOR COMPOUNDS THAT INTERFERE WITH FXI-T1 GENE PRODUCT MACROMOLECULE INTERACTION

FXI-T1 gene products of the invention may, in vivo, interact with one or more macromolecules, including intracellular macromolecules, such as proteins. Such macromolecules may include, but are not limited to, nucleic acid molecules and those proteins identified via methods such as those described, above. For purposes of this discussion, the macromolecules are referred to herein as "binding partners". Compounds that disrupt FXI-T1 binding in this way may be useful in regulating the activity of the FXI-T1 gene product, especially mutant FXI-T1 gene products. Such compounds may include, but are not limited to molecules such as peptides, and the like, as described, for example, which would be capable of gaining access to an FXI-T1 gene product.

The basic principle of the assay systems used to identify compounds that interfere with the interaction between the FXI-T1 gene product and its binding partner or partners involves preparing a reaction mixture containing the FXI-T1 gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of FXI-T1 gene product and its binding partner. Control reaction mixtures are incubated without the test compound or with a placebo. The formation of any complexes between the FXI-T1 gene protein and the binding partner is then detected. The formation of a complex in the control reaction, but not in the reaction mixture containing the test compound, indicates that the compound interferes with the interaction of the FXI-T1 gene protein and the interactive binding partner. Additionally, complex formation within reaction mixtures containing the test compound and normal FXI-T1 gene protein may also be compared to complex formation within reaction mixtures containing the test compound and a mutant FXI-T1 gene protein. This comparison may be important in those cases wherein it is desirable to identify compounds that disrupt interactions of mutant but not normal FXI-T1 gene proteins.

The assay for compounds that interfere with the interaction of the FXI-T1 gene products and binding partners can be conducted in a heterogeneous or homogeneous format. Heterogeneous assays involve anchoring either the FXI-T1 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the FXI-T1 gene products and the binding partners, e.g., by competition, can be identified by conducting the reaction in the presence of the test substance; i.e., by adding the test substance to the reaction mixture prior to or simultaneously with the FXI-T1 gene protein and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the FXI-T1 gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the FXI-T1 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of the FXI-T1 gene protein and the interactive binding partner is prepared in which either the FXI-T1 gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt FXI-T1 gene protein/binding partner interaction can be identified.

In a particular embodiment, the FXI-T1 gene product can be prepared for immobilization using recombinant DNA techniques described above. For example, the FXI-T1 coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above.

This antibody can be labeled with the radioactive isotope $^{125}$I, for example, by methods routinely practiced in the art. In a heterogeneous assay, e.g., the GST-FXI-T1 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the FXI-T1 gene protein and the interactive binding partner can be detected by measuring the amount of radioactivity that remains associated with the glutathione-agarose beads. A successful inhibition of the interaction by the test compound will result in a decrease in measured radioactivity.

Alternatively, the GST-FXI-T1 gene fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the FXI-T1 gene product/binding partner interaction can be detected by adding the labeled antibody and measuring the radioactivity associated with the beads.

In another embodiment of the invention, these same techniques can be employed using peptide fragments that correspond to the binding domains of the FXI-T1 protein and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments can be engineered to express peptide fragments of the protein, which can then be tested for binding activity and purified or synthesized.

For example, and not by way of limitation, a FXI-T1 gene product can be anchored to a solid material as described, above, in this Section by making a GST-FXI-T1 fusion protein and allowing it to bind to glutathione agarose beads. The interactive binding partner obtained can be labeled with a radioactive isotope, such as $^{35}$S, and cleaved with a proteolytic enzyme such as trypsin. Cleavage products can then be added to the anchored GST-FXI-T1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

5.16 INHIBITORY ANTISENSE, RIBOZYME AND TRIPLE HELIX APPROACHES

In another embodiment, symptoms of certain FXI-T1 disorders may be ameliorated by decreasing the level of FXI-T1 gene expression and/or FXI-T1 gene product activity by using FXI-T1 gene sequences in conjunction with well-known antisense, gene "knock-out," ribozyme and/or triple helix methods to decrease the level of FXI-T1 gene expression. Among the compounds that may exhibit the ability to modulate the activity, expression or synthesis of the FXI-T1 gene, including the ability to ameliorate the symptoms of a FXI-T1 disorder or a neuropsychiatric disorder, such as BAD, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the FXI-T1 gene could be used in an antisense approach to inhibit translation of endogenous FXI-T1 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-O-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–25 7451), etc. While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published October 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.1.1 GENE REPLACEMENT THERAPY

With respect to an increase in the level of normal FXI-T1 gene expression and/or FXI-T1 gene product activity, FXI-T1 gene nucleic acid sequences, described, above, can, for example, be utilized for the treatment of a FXI-T1 disorder or a neuropsychiatric disorder, such as BAD. Such treatment can be administered, for example, in the form of gene replacement therapy. Specifically, one or more copies of a normal FXI-T1 gene or a portion of the FXI-T1 gene that directs the production of a FXI-T1 gene product exhibiting normal FXI-T1 gene function, may be inserted into the appropriate cells within a patient, using vectors that include, but are not limited to adenovirus, adeno-associated virus, and retrovirus vectors, in addition to other particles that introduce DNA into cells, such as liposomes.

In another embodiment, techniques for delivery involve direct administration of such FXI-T1 gene sequences to the site of the cells in which the FXI-T1 gene sequences are to be expressed.

Additional methods that may be utilized to increase the overall level of FXI-T1 gene expression and/or FXI-T1 gene product activity include the introduction of appropriate FXI-T1-expressing cells, preferably autologous cells, into a patient at positions and in numbers that are sufficient to ameliorate the symptoms of a FXI-T1 disorder. Such cells may be either recombinant or non-recombinant.

Among the cells that can be administered to increase the overall level of FXI-T1 gene expression in a patient are normal cells that express the FXI-T1 gene.

Alternatively, cells, preferably autologous cells, can be engineered to express FXI-T1 gene sequences, and may then be introduced into a patient in positions appropriate for the amelioration of the symptoms of a FXI-T1 disorder. Alternately, cells that express an unimpaired FXI-T1 gene and that are from a MHC matched individual can be utilized. The expression of the FXI-T1 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399, 349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, that are capable of modulating FXI-T1 gene product activity can be administered using standard techniques that are well known to those of skill in the art. In instances in which the compounds to be administered are to involve an interaction with brain cells, the administration techniques should include well known ones that allow for a crossing of the blood-brain barrier.

5.17 PHARMACEUTICAL PREPARATIONS AND METHODS OF ADMINISTRATION

The compounds that are determined to affect FXI-T1 gene expression or gene product activity can be administered to a patient at therapeutically effective doses to treat or ameliorate a FXI-T1 disorder. A therapeutically effective dose refers to that amount of the compound sufficient to result in amelioration of symptoms of such a disorder.

5.1.2 EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.18 FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLES 6.1 Detection of FXI-T1 Homologs in Other Species by Southern Blot Southern Hybridization Under Test Conditions 7.5 $\mu$g of DNA samples from mouse (M), hamster (H), rabbit (R), bovine (B), monkey (Mo), human (Hu), and chicken (C) tissue samples were digested with EcoR1 and fractionated on a 0.8% agarose gel. The gel was blotted onto nitrocellulose filters (BA 85 Schleicher and Schuell). Prior to hybridization, filters are washed with 1× SSPE (1× SSPE: 180 mM NaCl, 10 mM NaPO$_4$, 1 mM EDTA) at 65° C. for 30 min., then prehybridized, at least 1 hr at 42° C., in 5× SSPE, 50% formamide, 1× Denhardts, and 0.5% SDS. (1× Denhardt's reagent is 0.02% Ficoll, 0.02% polyvinylpyrralodine, and 0.02% bovine serum albumin.) Preparation of nick-translated FXI-T1 cDNA probe is by standard protocols. Sambrook, J., et al., 1989, Molecular Cloning: A Laboratory Manual, 2nd ed. Cold Spring Harbor, N.Y.: Cold Spring Harbor Laboratory Press. Specific activity of probe is typically 1–5×108 cpm/$\mu$g; probe is used at a concentration of 1–3×10$^6$ cpm/ml hybridization solution. Filters are hybridized with 3×10$_6$ cpm/ml labeled p9.1(46) Eco probe (See FIG. 3), 16 hrs. at 42° C., in 5× SSPE, 50% formamide, 1× Denhardts, and 0.5% SDS and 5% dextran sulfate. After hybridization, filters are washed twice for 15 min at room temperature in 1× SSPE and 0.1% SDS, then washed twice for 15 min at 42° C. in 0.1× SSPE and 0.1% SDS, followed by 2 washes at 65° C. in 0.1× SSPE and 0.1% SDS. The filter was exposed to XAR-5 film with an intensifying screen at −70° C. for 24 hours.

Results

Hybridization signals were detected in all samples. The sizes of the bands visualized in each sample are as follows: mouse, 2 bands, a 4.2 kb and an 8.0 kb; hamster, 2 bands, a 6.6 kb and a 8.7 kb; rabbit, a 23 kb band; bovine, 3 bands, a 1.0, a 4.2, and an 8.0; monkey, 3 bands, a 3.7, a 7.7, and an 8.0; human, 3 bands, a 5.4, a 6.0, and a 9.0 kb; chicken, 3 bands, an 9.0, a 22, and a 23.

6.2 Isolation of cDNA Homologs of FXI-T1 in Other species

Tissue Selection

Northerns are performed using several different tissues from the organism of interest as the RNA source: brain, heart, kidney, liver, lung, skeletal muscle, spleen, thymus, testes, uterus, and ovary. RNA samples are fractionated in 1% agarose (Gibco BRL) gels and gel electrophoresis buffer containing 0.22 M formaldehyde. Tsang, S. S., et al., 1993, Biotechniques, 14:380–381. Gels are blotted onto maximum strength Nytran filters (Schleicher and Schuell); manufacturer's protocols are followed for blotting, hybridization and washing. Preparation of nick-translated FXI-T1 cDNA probe is by standard protocols. Sambrook, J., et al., 1989, Molecular Cloning: A Laboratory Manual, 2nd ed. Cold Spring Harbor, N.Y.: Cold Spring Harbor Laboratory Press. Specific activity of probe is typically 1–5×108 cpm/$\mu$g; probe is used at a concentration of 1–3×10$^6$ cpm/ml hybridization solution. To assess the quality and quantity of total RNA on Northern blots, filters are rehybridized with a 26-mer [$^{32}$P]ATP-labeled oligonucleotide, complementary to a species-conserved sequence of 28S ribosomal RNA, as described by Barbu and Dautry. Barbu, V., and Dautry, F., 1989, Nucleic Acids Res., 17:7115. Previous probes are stripped from filters according to the manufacturer's protocol. Filters are exposed to XAR-5 film with an intensifying screen at −70° C. Highest expression of FXI-T1 is found in skeletal muscle.

Construction of cDNA Libraries.

cDNA libraries are constructed in the $\lambda$Zap II vector (Stratagene; La Jolla, Calif.). Poly(A)+ RNA prepared from skeletal muscle is used to synthesize ds-cDNA according to the basic strategy of Gubler and Hoffman. Gubler, U., and Hoffman, B. J., 1983, Gene, 25:263–269. The synthesized ds-cDNA is blunt-end ligated with Eco RI/Xmn I Linker-adapters (prepared by annealing d(Eco RI-Xmn I) adaptor with complementary phosphorylated linker d(pXmn I)(New England BioLabs); and is both separated from excess linker-adapters and fractionated by size using Sepharose CL-4B chromatography (Pharmacia Biotech Inc.; Piscataway, N.J.). Pooled ds-cDNA fractions (>500 bp) are concentrated by EtOH precipitation and kinased with T4 polynucleotide kinase (Boehringer-Mannheim Biochemicals) prior to ligation with λZap II dephosphorylated Eco RI arms. The DNA is packaged using Gigapack Gold Extract (Stratagene) and transfected into XL1-Blue MRF' cells according to manufacturer's instructions. The cDNA library contains $1.3 \times 10^6$ pfu; 90% recombinants. The quality of the cDNA libraries is assessed by hybridization with (-actin cDNA sequences. Hagen, F. S., et al., 1988, Biotechniques, 6:340–345. Actin positive frequencies are >0.3% of recombinant pfu. Isolation of clones containing extended 5' mRNA sequences requires the construction of a random-hexamer primed library.

Library Screening

The λZap II FXI-induced cDNA library is plated at a density of $2-4 \times 10^3$ recombinant pfu per 15 cm plate in XL-1 Blue E.coli cells. A nitrocellulose filter (BA 85 Schleicher and Schuell; Keene, N.H.) replicas are made from each plate. The filters are denatured and neutralized by standard procedures. Sambrook, J., et al., 1989, Molecular Cloning: A Laboratory Manual, 2nd ed. Cold Spring Harbor, N.Y.: Cold Spring Harbor Laboratory Press. Filters are hybridized with cDNA probe prepared from an isolated fragment encoding murine FXI-T1. Prior to hybridization, filters are washed with 6× SSC (1× SSC: 150 mM NaCl, 15 mM NaCitrate) at 65° C. for 1 hr, then prehybridized, 4 hr at 65° C., in 6× SSC and 0.02% each of bovine serum albumin, polyvinylpyrrolidone and ficoll type 400 (Sigma Chemical Co.; St. Louis, Mo.). Filters are hybridized, 24–48 hr at 42° C., in 15 cm petri plates; 2.7 ml of hybridization solution is used per filter (50% formamide (Fisher Scientific; Pittsburgh, Pa.); 5× SSC; 5% dextran sulfate (Jersey Lab & Glove); 0.5% SDS (Gallard-Schlesinger Inds. Inc.; Carle Place, N.Y.); 10 µg/ml poly (A) (Pharmacia Biotech); 50 µg/ml denatured salmon sperm DNA (Sigma Chemical Co.); $1 \times 10^6$ cpm/ml labeled cDNA probe). After hybridization, filters are washed twice for 20 min at room temperature in 2× wash solution (2× SSC; 12 mM $Na_2HPO4$; 8 mM $NaH_2PO4$; 0.06% $Na_2$pyrophosphate; 0.05% SDS) followed by repeated washing at 65° C. in 1×, 0.4×, and 0.1× wash solution. To reduce background in long exposures, filters are then incubated in 0.1 M NaCl; 10 mM Tris/HCl pH8; 0.1 mM EDTA; 0.25% SDS and 0.2 mg/ml proteinase K for 1 hr at 37° C. followed by rinsing in 2× wash solution. Yancopoulos, G. D., et al., 1990, Proc. Nat'l. Acad. Sci. USA 87:5759–5763. Filters are exposed to Kodak XAR-5 (Eastman Kodak Co.; Rochester, N.Y.) film for 3 days, and again for 2 weeks, using an intensifying screen at −70° C. Plaques showing a positive hybridization signal with the FXI-thymoma cDNA probe are selected. Positive plaques are subcloned by excision with ExAssist helper phage. After screening approximately 10,000 recombinant phage, four positive clones are isolated.

6.3 Isolation of FXI-T1 from a human genomic DNA library gDNA library screening

A commercially obtained gDNA library is plated at a density of $2-4 \times 10^4$ recombinant pfu per 15 cm plate in E.coli cells. A nitrocellulose filter (BA 85 Schleicher and Schuell; Keene, N.H.) replicas are made from each plate. The filters are denatured and neutralized by standard procedures. Sambrook, J., et al., 1989, Molecular Cloning: A Laboratory Manual, 2nd ed. Cold Spring Harbor, N.Y.: Cold Spring Harbor Laboratory Press. Filters are hybridized with cDNA probe prepared from an isolated fragment encoding murine FXI-T1. Prior to hybridization, filters are washed with 6× SSC (1× SSC: 150 mM NaCl, 15 mM NaCitrate) at 65° C. for 1 hr, then prehybridized, 4 hr at 65° C., in 6× SSC and 0.02% each of bovine serum albumin, polyvinylpyrrolidone and ficoll type 400 (Sigma Chemical Co.; St. Louis, Mo.). Filters are hybridized, 24–48 hr at 42° C., in 15 cm petri plates; 2.7 ml of hybridization solution is used per filter (50% formamide (Fisher Scientific; Pittsburgh, Pa.); 5× SSC; 5% dextran sulfate (Jersey Lab & Glove); 0.5% SDS (Gallard-Schlesinger Inds. Inc.; Carle Place, N.Y.); 10 µg/ml poly (A) (Pharmacia Biotech); 50 µg/ml denatured salmon sperm DNA (Sigma Chemical Co.); $1 \times 10^6$ cpm/ml labeled cDNA probe). After hybridization, filters are washed twice for 20 min at room temperature in 2× wash solution (2× SSC; 12 mM $Na_2HPO4$; 8 mM $NaH_2PO4$; 0.06% $Na_2$pyrophosphate; 0.05% SDS) followed by repeated washing at 65° C. in 1×, 0.4×, and 0.1× wash solution. To reduce background in long exposures, filters are then incubated in 0.1 M NaCl; 10 mM Tris/HCl pH8; 0.1 mM EDTA; 0.25% SDS and 0.2 mg/ml proteinase K for 1 hr at 37° C. followed by rinsing in 2× wash solution. Yancopoulos, G. D., et al., 1990, Proc. Nat'l. Acad. Sci. USA 87:5759–5763. Filters are exposed to Kodak XAR-5 (Eastman Kodak Co.; Rochester, N.Y.) film for 3 days, and again for 2 weeks, using an intensifying screen at −70° C. Plaques showing a positive hybridization signal with the FXI-thymoma cDNA probe are selected. Positive plaques are subcloned. After re-screening, positive clones are isolated.

6.4 Assaying FXI-T1 Transcripts as a Predictor for X-irradiation Induced Leukemia PCR analysis Total RNA from tissue samples taken from X-irradiation exposed subjects are prepared using the Ologotex kit (Qiagen, Hildon Germany) and the kit provided protocol. Template cDNA is first prepared from mRNA in a reverse transcriptase reaction. 20 µl reactions contain the sample mRNA, 1× PCR buffer (0.5M KCl, 0.2M Tris-Cl pH 8.4, 25mM $MgCl_2$, 1 mg/ml bovine serum albumin), 1 mM each dNTP, 20 units Rnasin, and 200 units RTase. After a 60 minute incubation at 42° C., 80 µl 1× PCR buffer, 10–50 pmoles of upstream and downstream FXI-T1 specific primers and 1–2 units of Taq Polymerase are added. The samples are then amplified by repeated cycles of 95° C. denaturation for 1 minute, annealing at 55° C. for 1 min, and extension at 72° C. for 2 min. The reactions are analyzed by gel electrophoresis for the synthesis of expected bands. Amplification of control mRNA species, such as actin, allows normalization of RNA samples so that relative quantities of FXI-T1 mRNA transcripts can be determined.

6.5 Assaying FXI-T1 Transcripts as a Diagnostic for X-irradiation Induced Leukemia PCR analysis Total RNA from samples taken from subjects with a leukemia of unknown origin are prepared using the Ologotex kit (Qiagen, Hildon Germany) and the kit provided protocol. Template cDNA is first prepared from mRNA in a reverse transcriptase reaction. 20 µreactions contain the sample mRNA, 1× PCR buffer (0.5M KCl, 0.2M Tris-Cl pH 8.4, 25mM $MgCl_2$, 1 mg/ml bovine serum albumin), 1 mM each dNTP, 20 units Rnasin, and 200 units RTase. After a 60 minute incubation at 42° C., 80 µl 1× PCR buffer, 10–50 pmoles of upstream and downstream FXI-T1 specific prim ers and 1–2 units of Taq Polymerase are added. The samples are then amplified by repeated cycles of 95° C. denaturation for 1 minute, annealing at 55° C. for 1 min, and extension at 72° C. for 2 min. The reactions are analyzed by gel electrophoresis for the synthesis of expected bands. Amplification of control mRNA species, such as actin, allows normalization of RNA samples so that relative quantities of FXI-T1 mRNA transcripts can be determined.

We claim:

1. An isolated FXI-T1 nucleic acid which hybridizes under moderately stringent conditions to a nucleic acid having the sequence of SEQ ID NO:2 or a complement of said nucleic acid.

2. The nucleic acid of claim 1, wherein the FXI-T1 gene is a murine FXI-T1 gene.

3. The nucleic acid of claim 2, having a sequence which is SEQ ID:2.

4. The nucleic acid of claim 2, having a sequence which is SEQ ID:3.

5. The nucleic acid of claim 1, wherein the FXI-T1 gene is a human FXI-T1 gene.

6. The nucleic acid of claim 1, which further comprises a label.

7. The nucleic acid of claim 1, which is a ribonucleic acid.

8. The nucleic acid of claim 1, which is a deoxyribonucleic acid.

9. A method of classifying a sample of tissue which comprises comparing the level of FXI-T1 expression by nucleic acid hybridization in tissue sample with the level of FXI-T1 expression in a standard tissue.

10. An isolated FXI-T1 nucleic acid which hybridizes under highly stringent conditions to a nucleic acid having the sequence of SEQ ID NO:2 or a complement of said nucleic acid.

* * * * *